US010288614B2

(12) United States Patent
Basinger, Jr. et al.

(10) Patent No.: US 10,288,614 B2
(45) Date of Patent: May 14, 2019

(54) DETECTION OF THE DEGREE OF EXPOSURE TO CHEMICAL WARFARE NERVE AGENTS AND ORGANOPHOSPHATE PESTICIDES WITH LATERAL FLOW ASSAYS

(71) Applicants: G. William Basinger, Jr., Charlotte, NC (US); Kristin H. Clement, Cornelius, NC (US)

(72) Inventors: G. William Basinger, Jr., Charlotte, NC (US); Kristin H. Clement, Cornelius, NC (US)

(73) Assignee: Countervail Corporation, Charlotte, NC (US)

( * ) Notice: Subject to any disclaimer, the term of this patent is extended or adjusted under 35 U.S.C. 154(b) by 376 days.

(21) Appl. No.: 15/191,806

(22) Filed: Jun. 24, 2016

(65) Prior Publication Data

US 2016/0377617 A1  Dec. 29, 2016

Related U.S. Application Data

(60) Provisional application No. 62/183,893, filed on Jun. 24, 2015.

(51) Int. Cl.
*G01N 33/573* (2006.01)
(52) U.S. Cl.
CPC .... *G01N 33/573* (2013.01); *C12Y 301/01007* (2013.01); *C12Y 301/01008* (2013.01); *G01N 2333/918* (2013.01); *G01N 2440/14* (2013.01)

(58) Field of Classification Search
None
See application file for complete search history.

(56) References Cited

U.S. PATENT DOCUMENTS 9,977,018 B2 *  5/2018  Marks ............... G01N 33/5438
2017/0336398 A1 * 11/2017  Lin .................. G01N 33/54346

OTHER PUBLICATIONS

Du et al. Analytical Chem. 2012 84: 1380-1385 (Year: 2012).*
Liu et al. Chemistry 2008 14: 9951-9956 (Year: 2008).*
Periasamy et al. Sensors 2009 9: 4034-4055 (Year: 2009).*

* cited by examiner

*Primary Examiner* — Changhwa J Cheu
(74) *Attorney, Agent, or Firm* — Blake E. Vande Garde; Erickson Kernell IP, LLC

(57) ABSTRACT

A sample analysis device used to detect a level of exposure of organophosphorus within a sample comprising a sample collection pad, at least one conjugate zone comprising an anti-analyte antibody that is conjugated with a reporter label, and a control antibody that is conjugated with a reporter label, a blocking and/or test zone comprising an immobilized nanoparticle or other molecule that captures the Organophosphate-bound analyte, a second blocking and/or test zone comprising an immobilized antibody that binds to the unbound analyte and an optional third blocking and/or control zone comprising an immobilized antibody that binds to the control molecule wherein, when the analyte is bound by the Organophosphate in the sample it will bind to the first test line, and if the analyte is "free' from the Organophosphate it will bind to the second test line, and the control antibody will bind to the control line.

18 Claims, 3 Drawing Sheets

Diagram of methods of detection, or reading the device to interpret results in a preferred embodiment.

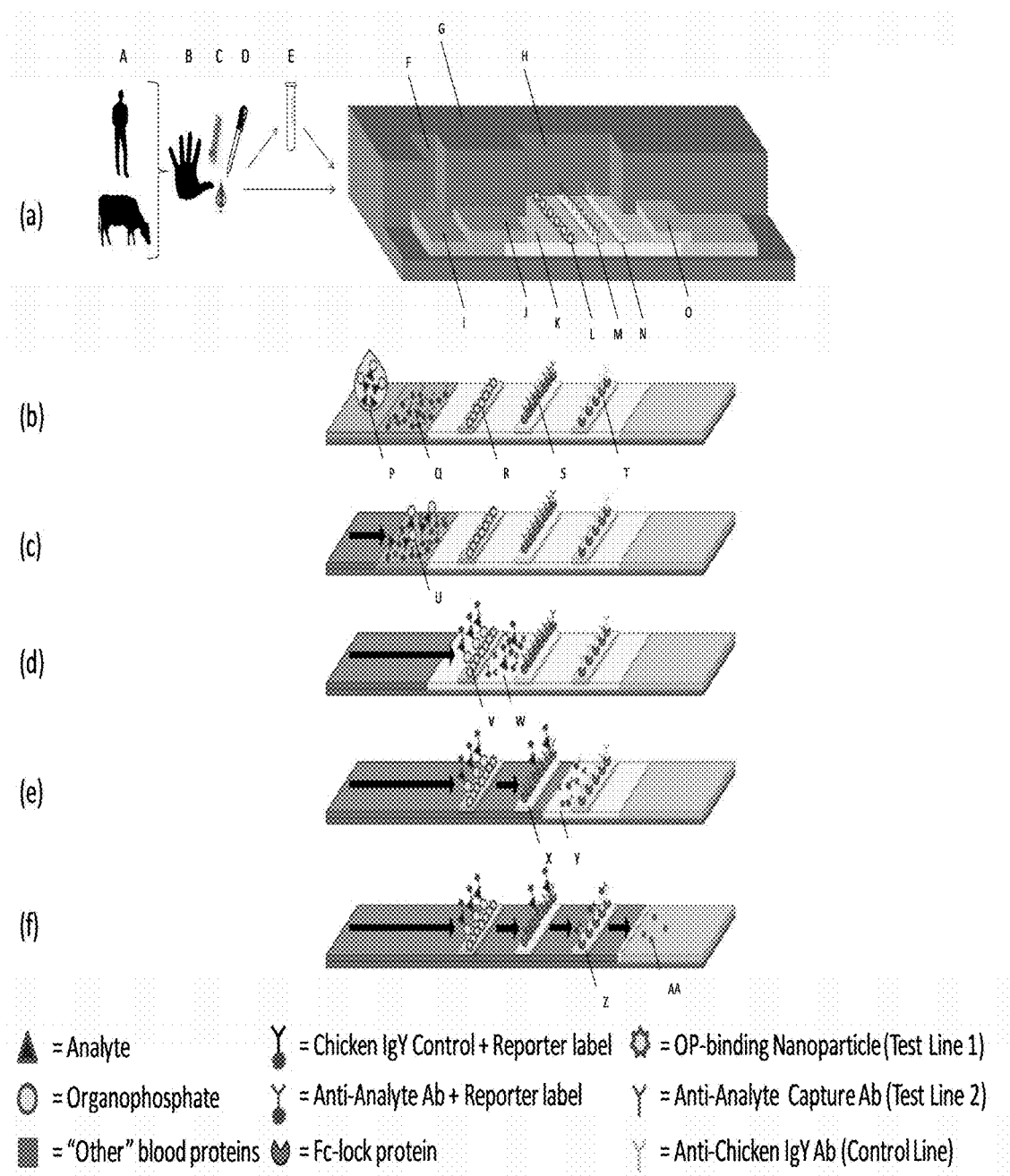
FIG. 1 Diagram of the lateral flow strip device in a preferred embodiment.

FIG. 2 Diagram of methods of detection, or reading the device to interpret results in a preferred embodiment.
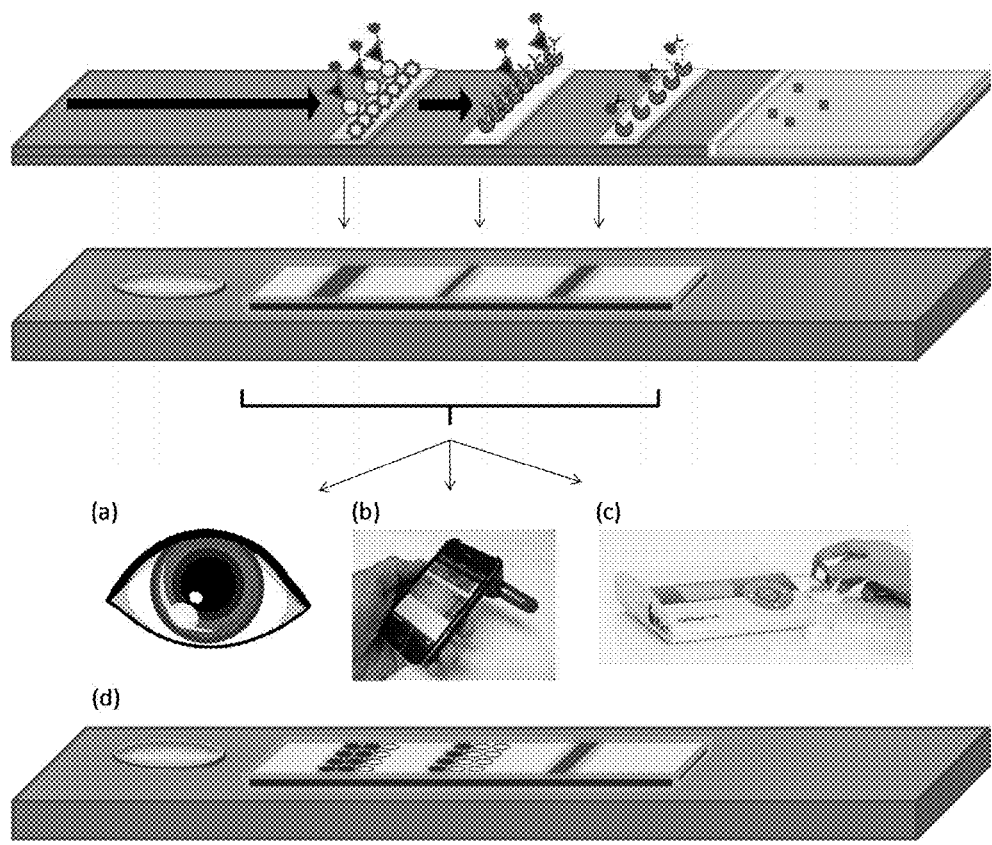

FIG. 3 Diagram of the dipstick detection device in a preferred embodiment.
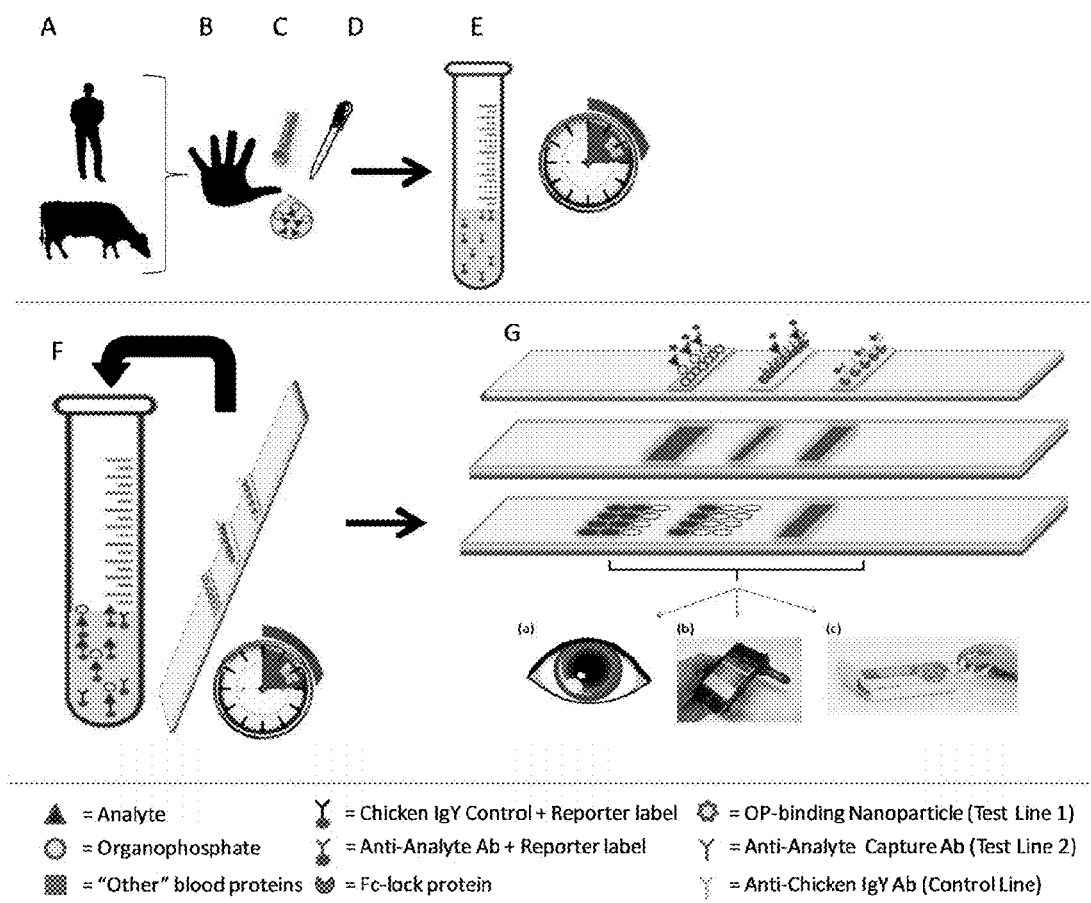

DETECTION OF THE DEGREE OF EXPOSURE TO CHEMICAL WARFARE NERVE AGENTS AND ORGANOPHOSPHATE PESTICIDES WITH LATERAL FLOW ASSAYS

RELATED CASES

This application claims the priority of the provisional application Ser. No. 62/183,893 filed Jun. 24, 2015. Applicant hereby incorporates by reference the entire content of provisional application Ser. No. 62/183,893.

FIELD OF INVENTION

The present invention relates to the field of medical testing devices and their methods of use, lateral flow (immune) assays (LFA), dipstick assays, and field deployable assays. In particular, the invention pertains to measuring the degree of exposure to chemical warfare nerve agents and organophosphate (OP) pesticides in a baseline-free manner via a ratio of OP bound cholinesterase vs. non-OP bound cholinesterase in human or animal samples.

BACKGROUND OF THE INVENTION

Nerve agents and a large number of pesticides fall into a class of chemicals called organophosphates (OP), which pose serious health concerns for military and civilian populations alike. OP-pesticide compounds are commercially available and abundantly used worldwide. In addition to hazards associated with routine, chronic, low-level exposure over time, misuse of OP-pesticides has also led to malicious, suicidal, or accidental acute intoxications; the repercussions of which (chronic and acute alike) lead to life-long and debilitating neurological deficits. Although OP pesticide use in the United States is declining, malathion is widely used in agriculture, residential landscaping, public recreation areas, and in public health pest control programs such as mosquito eradication (US EPA, 2007, Bonner 2007). Forty OP pesticides are registered in the U.S., with at least 73 million pounds used in agricultural and residential settings (Maugh 2010). According to the World Health Organization (WHO), more than one million serious accidental, and two million suicidal poisonings with pesticides occur worldwide every year (Jeyaratnam 1990). In rural regions of developing countries, suicide via OP pesticides kills ~200 000 people per year. Unintentional poisoning kills fewer people, but is a still problem where highly toxic OP pesticides are available (Eddleston 2008).

In addition to OP-pesticides, tactical use of OP-nerve agents (chemical weapons, such as sarin, soman, Tabun, and VX to name a few) against the warfighter as well as non-military personnel is a potentially imminent and legitimate deadly threat. Radical political groups and unstable governments have successfully deployed nerve agents in the recent past. Tabun was used by the Iraqi military against Iran in the 1980s, and sarin was used by the terrorist group Aum Shinrikyo in the Matsumoto and Tokyo subways in the mid-1990s (Nozaki H 1995) (Macilwain 1993) (Brown M A 1998). The United Nations investigation of allegations against the Syrian Arab Republic confirmed "unequivocally and objectively" that chemical weapons were used in the Ghouta area of Damascus in Syria on Aug. 21, 2013 (Sellstrom A 2013). During these events, surface-to-surface rockets containing the nerve agent sarin were utilized. Within three hours of the attack, three hospitals in the Damascus area received approximately 3,600 patients displaying symptoms consistent with nerve agent exposure. From this event, it is estimated that there were approximately 1429 deaths, 426 of which were children (The White House 2013). Most recently, the International Business Times reported (Feb. 22, 2015) that, "Islamic State Fighters in Libya may have seized large amounts of chemical weapons, including mustard gas and the nerve agent Sarin." "The ISIS Fighters near Tripoli have begun testing the weapons that reportedly once belonged to the former regime of Moammar Gadhafi. 'Before his death, Gadhafi left approximately 1,000 cubic tons worth of material used for manufacturing chemical weapons and about 20,000 cubic tons of mustard gas.'" Taken together, in addition to the pervasive use of dangerous OP pesticides worldwide, it is also highly plausible that OPs may be used again in the future with malicious intent.

The prolific use of OP-pesticides worldwide coupled with a serious homeland security concern that OP-based nerve agents may be deployed either against our troops or civilians on our home soil has stimulated the search for rapid, miniaturized and inexpensive point-of-care diagnostic devices for first responders and medical personnel to detect the degree of exposure (Langenberg 2009). Taken together, there is an unmet need to rapidly identify patients that have been exposed to OP toxicants and determine degree of exposure, particularly at lower exposure levels. Lower OP exposure produces vague, nondescript signs and symptoms that are not easily differentiated from other conditions. The lack of an accurate diagnosis of some exposure to OP agents may result in a delay, or complete lack of receipt of needed treatment, the use of life-endangering resuscitation drugs, or the use of high risk anesthetics that can cause injury or death in those who have been exposed to OP agents. In the event of a military or terrorist release of a chemical warfare nerve agent, the analysis of biomedical samples for the presence of biomarkers to confirm exposure is imperative to ensure that appropriate medical countermeasures are administered in a timely manner. In addition to identifying those with true nerve agent poisoning (both apparent and subclinical, also referred to as the "walking wounded"), it is important to verify non-exposure to reassure worried civilian or military personnel (also referred to as the "worried well") (Sambursky 2015).

Specific diagnostics to identify exposure to OPs were rapidly developed following the attacks in Japan in the mid-1990s. Assays that measured metabolites to identify the exact OP agent relied on acid hydrolysis products in urine. However, because OP compounds are unstable in pure aqueous solutions and are rapidly degraded upon entering the body, the urinary metabolites are excreted very rapidly and are not practical for retrospective OP exposure analysis (Driskell 2002) (Shih 1994). Therefore, analysis for the presence of intact OP agents in blood is inappropriate unless samples are collected immediately after exposure.

However, upon entering the body via inhalation or skin absorption, OP agents enter the blood and immediately combine with blood proteins to form blood protein-nerve agent adducts. Specifically, OPs irreversibly complex with both acetylcholinesterase (AChE) and butylcholinesterase (BChE) enzymes. AChE and BChE enzyme activity are good biomarkers for risk assessment because they not only substantiate exposure, but also directly provide a quantitative biochemical effect of the exposure (i.e., enzyme inhibition). Furthermore, these biomarkers of exposure are persistent at least 16 days post-exposure, likely much longer (Fidder 2002) (Solano 2008).

Numerous methods have been developed to assess AChE and/or BChE levels, including the Ellman assay, fluorescence assay, electrochemical assay, Michel (ΔpH) ChE assay, radioactive assay, and Walter Reed Army Institute of Research (WRAIR) assay. The Model 400 Test-Mate™ ChE assay kit, which uses enzyme activity for screening of OP exposure is FDA-approved and commercially available. All of these methods are based on detecting a meaningful decrease in enzyme activity from a previously established baseline, which can vary depending on the testing method (Haigh J R 2008).

AChE is a protease found primarily in the brain and red blood cells and is responsible for breaking down the neurotransmitter acetylcholine (ACh) at the cholinergic synapses in the Central and Peripheral Nervous Systems (CNS/PNS) and at neuromuscular junctions. Inhibition of AChE by an OP leads to the accumulation of ACh and excessive stimulation of the CNS/PNS. When ACh levels reach a critical threshold, classic symptoms of cholinergic crises appear such as miosis, nausea, vomiting and diarrhea, hypersecretions, difficulty breathing, and death in extreme cases.

The diagnostic described herein seeks to capitalize on the finding that the degree of AChE or BChE inhibition is directly proportional to the extent of OP-exposure. The AChE enzyme has three isoforms produced by alternative splicing of pre-mRNA: synaptic isoform (AChE-S) is produced and found primarily in brain and muscle tissues, erythrocytic isoform (AChE-E) is anchored to red blood cell (RBS) membranes. Since it is very invasive to obtain AChE-S, measurement of AChE-E is usually sampled as a surrogate indicator of AChE inhibition in the CNS/PNS (Knechtges 2008). BChE is readily found in plasma but the biological role of BChE is not fully understood. Although BChE also hydrolyzes ACh, it is primarily recognized as a scavenging enzyme for detoxification of naturally-occurring compounds (Lotti 1995) (Poet T S 2003) (Shen Z 2004).

In the past several years, numerous groups have independently demonstrated that there is a statistically significant correlation of BChE inhibition to measurable signs and symptoms of OP intoxication as scored by various poisoning classification systems (e.g. Glasgow Coma Scale, APACHE II, Proudfoot classification, and Peradenya Organophosphorus Poisoning Scale) (Prasad D R M M 2013, Kumar C U 2014, Ahmed K M 2014, Patil G 2015, Patil S L 2014, Sungertekin, H 2006) Additionally, BChE is easily extracted and measured from plasma (Li 2010), has a high rate of reaction, and is vastly more abundant (10-500 times) than AChE (Nigg H N 2000) (Holland K D 2008) (Solano 2008). Taken together, either AChE or BChE serves as an excellent direct or indirect biomarker, respectively, for OP exposure (Prasad DRMM 2013), (Haigh J R 2008).

However, measurement of cholinesterase (both AChE and BChE) is complicated by inter- and intra-individual variability of ChE activity and relationship to clinical signs and symptoms. The variability of AChE activity between individuals based simply on genetics, sex, race, or age is estimated as high as 23% (Lessenger J E 1999). The deviation of BChE from mean is up to 65% (Knaak J S 2012). This level of cholinesterase (ChE) population variation underscores the importance of having individual baseline values of ChE activity to interpret results when assessing exposures to ChE-inhibitors. In the absence of a baseline (which is likely the case in the event of a mass casualty scenario) ChE inhibition measurements are often based on a population average that introduces a large degree of uncertainty caused by the enzyme variability within the population. These uncertainties reduce the sensitivity of AChE/BChE activity as a biomarker and thus may provide ambiguous results for subclinical, low-dose OP exposure (<20% enzyme inhibition). However, cholinesterase inhibition may be subclinical in appearance only, as there is evidence that even a low dose exposure of OP neurotoxicants can cause long-term, significant chronic neurological deficits (McDonough J H 1997) (Abou-Donia 2003) (Chen 2012).

Recent advances in the application of nanomaterials as transducers, recognition agents or labels, and advances in immunoassay techniques are now being exploited in the design of improved devices for the biomedical detection of non-metabolized OP pesticides and nerve agents, metabolites, and protein adducts (Black R M 2013). Several laboratories have developed techniques that approach meeting various diagnostic needs of OP exposure, but each method is caveated with drawbacks. Some recent examples include:

Zhang et al., (2013) developed a lateral flow assay test strip that detects OP-AChE adducts by selectively capturing the AChE with quantum dot (Qdot)-tagged anti-AChE antibodies and zirconia nanoparticles ($ZrO_2$). A sandwich of Qdot-Anti-AChE Ab/OP-AChE/$ZrO_2$ was detected using a hand-held fluorescence detector. Lu et al. (2011) also utilized $ZrO_2$ nanoparticles to bind BChE from plasma in a disposable electrochemical immunosensor. The drawback to both of these approaches is that only OP-bound AChE or BChE levels were detected yielding a quantitative response that, in the absence of a baseline, are challenging to interpret (Zhang W 2013).

Du et al. and Ge et al. (2011 and 2013) developed both an integrated lateral flow test strip with an electro-chemical sensor (LFTSSES) and an electrochemical method using $Fe_3O_4$/Au nanocomposites resulting in rapid, selective, and sensitive quantitation of OP exposure based on parallel measurements of both OP-AChE and reactivated AChE (using treatment with the oxime 2-PAM). Even though these methods attempted a baseline-free approach, both systems rely on the reactivator (oxime) to strip the OP from the AChE molecule to generate baseline levels of enzyme. These approaches are not compatible for all OP exposures in which the phosphorylated AChE or BChE can either spontaneously regenerate, or have aged to the point of permanent OP-adduction (Du D 2011) (Ge X. 2013).

Dr. Rudolph Johnson laboratory developed and optimized a baseline-free approach to measuring OP-bound and free BChE using immunomagnetic separation couple with liquid chromatography tandem mass spectrometry (LC-MS/MS). The optimized method captures >88% of the BChE in a specimen. The drawback to this method is that it is laboratory-based requiring trained personnel to perform specialized sample extractions and operation of sophisticated instruments (Knaak J S 2012) (Pantazides B G 2014).

Test-mate ChE Cholinesterase Test System (Model 400) is a commercially available product from EQM Research, Inc. for determining the percentage of active Acetylcholinesterase or Butyrylcholinesterase. The system utilizes a microwell format with a small fixed wavelength photometer to read results. The test method is based on the conventional Ellman assay which has the innate drawback of the requirement of a baseline result in order to accurately determine the degree of cholinesterase inhibition in a test subject. A secondary drawback of the system for point of care field use is that it is designed for use in a clinical laboratory by a medical technician under supervision of a laboratory director.

SUMMARY OF THE INVENTION

A sample analysis device used to detect a level of exposure of organophosphorus within a sample comprising a sample collection pad, at least one conjugate zone comprising an anti-analyte antibody that is conjugated with a reporter label, and a control antibody that is conjugated with a reporter label, a blocking and/or test zone comprising an immobilized nanoparticle or other molecule that captures the Organophosphate-bound analyte, a second blocking and/or test zone comprising an immobilized antibody that binds to the unbound analyte and an optional third blocking and/or control zone comprising an immobilized antibody that binds to the control molecule wherein, when the analyte is bound by the Organophosphate in the sample it will bind to the first test line, and if the analyte is "free' from the Organophosphate it will bind to the second test line, and the control antibody will bind to the control line.

A method of detecting a level of exposure to an organophosphorus compound via measurement of OP-bound and unbound cholinesterase levels in a sample, comprising the steps of: (a) collecting a sample; (b) transferring the sample to a sample analysis device, the device comprising a sample collection pad, at least one conjugate zone comprising an anti-analyte antibody that is conjugated with a reporter label, and a control antibody that is conjugated with a reporter label, a blocking and/or test zone comprising an immobilized nanoparticle or other molecule that captures the Organophosphate-bound analyte, a second blocking and/or test zone comprising an immobilized antibody that binds to the unbound analyte and an optional third blocking and/or control zone comprising an immobilized antibody that binds to the control molecule; wherein, when the analyte is bound by the Organophosphate in the sample it will bind to the first test line, and if the analyte is "free' from the Organophosphate it will bind to the second test line, and the control antibody will bind to the control line; (c) detecting both the presence or absence of the binding molecule in the first test zone and the remaining analyte in the second test zone to culminate reporting a ratio of bound- and free-analyte and (d) determining the level of OP exposure for an individual.

BRIEF DESCRIPTION OF THE DRAWINGS

FIG. 1 Diagram of the lateral flow strip device
FIG. 2 Diagram of methods of detection, or reading the device to interpret results.
FIG. 3 Diagram of the dipstick detection device

DETAILED DESCRIPTION OF THE INVENTION

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The invention described herein is an innovative, never before seen device that is broad-spectrum for all OP compounds (nerve agents and OP pesticides alike), user-friendly for novices, quantitative and informative for medical personnel, rugged and stable for field deployment, inexpensive, and marketable to both government and private sector for medical and veterinary uses. This technology also can be expanded to detect exposure to carbamate-compound exposures.

The invention combines the sophistication of nanoparticle and reporter labeling technology with the simplicity of a lateral flow test strip or dipstick technology. This approach accomplishes producing a one-step or two-step, broad-OP-spectrum, baseline-free assessment of cholinesterase inhibition without requiring sophisticated laboratory equipment. The resulting device will address a key clinical need of determining degree of OP exposure while providing the simplicity and rapid assessment of a point of care baseline free diagnostic format.

For the sake of simplicity, we will refer to the analyte as cholinesterase (ChE) since either AChE or BChE may be the target analyte of interest. This device will multiplex binding OP-adducted ChE and free-ChE from OP-containing blood samples using a lateral flow (LF) cassette with a one or two-step buffer delivery system. The first step will separate OP-adducted and free ChE, and the second step will label the test lines with a reporter molecule. Briefly, a metered amount of whole blood may be added directly to the device, or separated to plasma using an on-board filter. Next, the sample will run through the cassette whereby OP-ChE adducts will be separated from free ChE. Specifically, the first capture line is comprised of zirconium dioxide ($ZrO_2$) nanoparticles which will tightly bind to any OP moiety, thus capturing the OP-ChE adducts. The remaining free-ChE will pass the first line and bind to a second capture line containing anti-ChE specific antibodies. If needed, a chase buffer (housed in an on-board blister pouch or another mechanism to separate the buffer, such as an ampoule) containing a second, anti-ChE antibody (matched pair to the capture Ab) conjugated to a visible particle will pass through the entire cassette and label any ChE bound to either test line. Any user of the device (seeking CLIA-waiver for use by an untrained novice without a reader) can discern immediately if some level of exposure has occurred (based on detection of a single positive line as "unexposed," and two positive lines as "OP-exposed") prompting him/her to seek further medical attention. Further, if the user has access to a hand-held reader, a quantitative percentage of ChE inhibition by comparing the signal intensity of the reaction lines may be coupled with tiered treatment recommendations. This device can also serve as a companion diagnostic to FDA-approved conventional care OP-therapies such as the DuoDote auto-injectors housing atropine-plus-2-PAM.

This invention pertains to a rapid, point-of-care assay and method to detect organophosphate (OP) poisoning via measurement of OP-bound and free cholinesterase after exposure to nerve agents, OP-pesticides and other OP-based chemicals. In some preferred embodiments, the assays are direct sandwich assays. The test preferably utilizes either a finger stick peripheral blood, plasma, or serum specimen.

The invention described in this application is a baseline free, rugged, field-deployable point-of-care (POC) device that detects the degree of exposure to OP neurotoxicants based upon the determination of ChE inhibition via the simultaneous measurement of OP bound and unbound ChE. A conjugated label can be used that is both visible by the naked eye (such as colored latex particles or colloidal gold), and also provides sufficient contrast (e.g. via fluorescence, luminescence, or color intensity from colloidal gold or cellulose nanobeads) that may be quantitative when scanned by a hand-held instrumented reader or other reading device. Examples of a handheld reader include an existing lateral flow reader system from LRE (cPOC) or Qiagen Lake Constance (ESEQuant). The reader will be a small, easy-to-use fluorescence, luminescence, or color measurement system that is sensitive to the presence of fluorescent or other markers, robust and capable of withstanding punishment in the field, and cost-effective. For example, a fluorescence reader would include a detector with a light-emitting diode (LED) and filter technology, and tube scanner to detect fluorescent markers comparable to commercial spectrophotometers. The reader would include a customizable user interface and LIS (Laboratory Information System) and HIS (Hospital Information System) connectivity and enables connection to cloud-based applications. Comparison of signal intensity between the two reaction lines (i.e., OP-bound ChE and unbound ChE), is used to determine the result.

The appeal of the option for using a dual-potential label (readable by both the naked eye and by an instrumented reader) is that any user of the device (even if an untrained novice without a reader) can discern immediately if some level of exposure has occurred (e.g. based on detection of 1 line as unexposed, and 2 lines as some degree of OP-exposure) prompting him/her to seek further medical attention. Further, if the user has access to a hand-held reader or other reading device, the ratio of OP-bound/free ChE as determined by comparing the signal intensity between the two reaction lines may be used to compute a percentage of cholinesterase inhibition that may be used to evaluate the degree of exposure and aid in decisions for providing treatment The device that we conceptualize is highly innovative and impactful at many levels. For starters, this rapid test will be useful in the differential diagnosis of OP exposure by clinicians in the event a patient presents to an emergency room with signs and symptoms that appear like a cholinergic crisis, but OP exposure is not known. For example, falsely depressed levels of AChE occur with pernicious anemia and hemoglobinopathies, and falsely depressed levels of BChE occur with liver dysfunction, pregnancy, use of certain drugs (e.g. codeine, morphine), and many more (Katz 2015). Toxicity with non-OP agents such as carbamates, nicotine, mushroom poisoning, botulism, and numerous agents can be confused with OP-exposure as they present with very similar signs and symptoms (Katz 2015). These disorders would present like a cholinergic crisis (or actually would be a cholinergic event) but would be unrelated to OP exposure. Therefore, a rapid test to clearly confirm OP-toxicity, as our invention would, (with an OP-positive test line) is critical, as standard care therapy for OP exposure with atropine-plus-2-PAM can be toxic if OP-exposure did not actually occur (Leikin 2002).

In a mass casualty or emergency event, our device will be simple enough to allow for self screening by potentially exposed victims to alleviate resource demands on first responders. The read-out of the device will be simple to interpret: one positive line equals "negative," and two positive lines equals "positive" to some degree of OP exposure (not including the control line). With a visually read positive result (positive OP-ChE test line, or "Test line 1"), the victim would be prompted to seek appropriate medical attention. The intensity of binding to each test line reflects degree of exposure. The ratio of label signal intensities can be quantitated by a handheld reader. "Light" binding to the first line (for OP-ChE) and "heavy" binding to the second (for free ChE) represents mild OP exposure, whereas "heavy" binding to the first line relative to the second reflects substantial OP exposure. No binding to the first line followed by heavy binding to the second line represents no OP-exposure, which may mean that the victim possibly displaying cholinergic signs and symptoms was exposed to a non-OP toxicant, such as the disorders described above. First responders using a hand-held reader will benefit from the quantitative aspects of the diagnostic device to assist in the treatment decisions. This device is intended to give a rapid result (target <4-5 min), and maintain an accurate signal lasting long enough for a quantitative instrumented reading, even up to 24 hours later.

Finally, this device also may be used for evaluating occupational or agricultural exposure. Specifically, chronic or acute exposures may occur with industrial agricultural workers, manufacturing industry workers, pesticide exterminators, greenhouse workers, etc. This diagnostic may also be marketed to those concerned with environmental or non-occupational/residential exposure (resident or exterminator use, dietary exposure, accidental exposure), close proximity to farms with or without aerial spraying, and suicide attempt. A goal during development is to identify antibodies that are cross reactive with animal ChE, to take advantage of veterinary market applications for livestock and companion animals exposed to OP compounds.

Lateral flow (immuno)assays (LFA) are currently used for qualitative, semi-quantitative and to some extent quantitative monitoring in resource-poor or non-laboratory environments, and are important for diagnostic purposes. Lateral flow assays are typically prefabricated strips of a carrier material containing dry reagents that are activated by applying the fluid sample. In a similar genre of diagnostic tests are dipstick assays, which are based upon immunoblotting principles. Dipstick assays do not rely on lateral fluid flow through a membrane, but for the purposes of the invention described herein, dipstick assays are appropriate to reference as they embody necessary protein-protein binding properties to isolate and label target proteins from a complex biological milieu.

For the purposes of this invention, whole blood/plasma/serum from either humans or animals is the preferred sample matrix. This permits rapid screening of a large at-risk population at the event scene. Organophosphate agents are immediately detectable within a few minutes after exposure, and have a long lasting detection window (days) by detection of OP-adducts with cholinesterase. Obtaining a blood sample is non-invasive. While other sample matrices could be used, they are not as preferred. For example, urine has a time lag for detectable markers to appear. Metabolites and hydrolysis products are only present in body fluids in very low concentrations after exposure. Collection of a cerebrospinal fluid (CSF) sample is invasive and not point-of-care (Sambursky 2015).

An organophosphate (OP) or phosphate ester is the general name for esters of phosphoric acid. Organophosphates are the basis of many insecticides, herbicides, and nerve agents. Organophosphate poisoning results from exposure to organophosphates, which cause the inhibition of acetylcholinesterase (AChE), leading to the accumulation of acetylcholine (ACh) in the body.

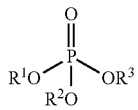

Chemical Structure of Organophosphates

Carbamate refers to an organic compound derived from carbamic acid ($NH_2COOH$) or their salts.

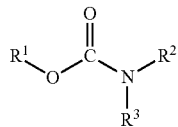

Chemical Structure of Carbamates

Looking now to the Figures where like numerals indicate like items, various embodiments of elements of the instant invention are illustrated. Looking first to FIG. 1, this diagram depicts one design of the lateral flow test strip device, with the following components:
A: Sample is obtained from either human or animal
B: Human sample is obtained from a finger stick
C: A disposable lancet is used to obtained sample
D: A disposable pipette is used to transfer sample to device or sample tube
E: Sample may be pre-diluted into a buffer, or transferred directly to the device
F: Sample inlet
G: Plastic housing
H: Detection window
I: Sample pad
J: Conjugation pad
K: Incubation and detection pad
L: Test Line 1
M: Test Line 2
N: Control Line
O: Absorbent pad
P: Sample is added through sample inlet to sample pad
Q: Conjugation pad is comprised of labeled antibodies against the analyte or a labeled control antibody
R: Test Line 1 comprised of OP-binding nanoparticles
S: Test Line 2 comprised of anchored anti-analyte antibodies (possibly anchored with Fc-binding protein)
T: Control line comprised of anchored antibodies to the control antibody (possibly anchored with Fc-binding protein)
U: Labeling of the analyte on the conjugation pad
V: OP-adducted analyte binds to the Test Line 1
W: All other molecules flow past, including un-adducted analyte
X: Un-adducted analyte binds to Test Line 2
Y: All non-analyte molecules flow past
Z: Control antibody is captured on the Control Line
AA: Remaining molecules flow past Taking a closer look at FIG. 1, steps a-f, with individual components labels A-AA. For use in a LFA, the preferred embodiment is to collect a finger-stick blood sample from potentially exposed humans by using a disposable lancet or whole blood collection delivery device that may directly interlock with the lateral flow device (FIG. 1, A, B, C), and in other embodiments, from animals (FIG. 1, A). If the sample is not delivered via an interlocking device, the sample is transferred with a disposable pipette (FIG. 1, D) either to a tube containing an intermediate dilution buffer or a sample prep device and then transferred to the sample pad of the device, or alternatively, the blood sample is added to the sample pad directly (FIG. 1, E). The sample is transferred to the device sample inlet (FIG. 1, F), which is optionally enclosed in a plastic or other suitable housing, (FIG. 1), G. If using a whole blood delivery device that interlocks, attachment of the collection device will actuate the running buffer to deliver whole blood directly to the cassette, where the blood+running buffer would then pass through a filter stack using established depth filters such as Vivid, Cytosep (Pall), MF1, or VF2 (GE). Exclusion of blood cells may be advantageous if the target analyte is BChE as it excludes AChE (found on red blood cells), improving selectivity for BChE. The device is comprised of a detection window, sample pad, conjugate pad, incubation and detection pad, Test Line 1, Test Line 2, Control Line, and an absorbent pad (FIGS. 1, H, I, J, K, L, M, N, and O, respectively). Not shown in FIG. 1, but potentially may be used is a blister pouch (or equivalent mechanism) to serve as containment for an on-board "chase buffer" if the device requires a two-step separation/detection system.

Specifically, in a preferred embodiment, the conjugation pad is comprised of anti-analyte and control molecules (e.g., control antibodies, both conjugated with a reporter label (FIG. 1, Q). In other embodiments, the reporter molecule is conjugated to a anti-ChE detection antibody and housed in an on-board foil blister pouch (or equivalent, such as an ampule) that is secondarily released as a "chase buffer" to label the test lines after the OP-bound and free ChE have been separated on the Test Lines. Test Line 1 is comprised of an OP-binding nanoparticle or other OP binding component (FIG. 1, R), Test Line 2 is comprised of an anti-analyte capture antibody, possibly anchored with an Fc-binding protein (FIG. 1, S), and the Control Line is comprised of an anti-control antibody, possibly anchored with an Fc-binding protein (FIG. 1, T).

Via capillary action of nitrocellulose in the preferred embodiment (and PVDF, Fusion 5, or other lateral flow matrix technology in other embodiments), the whole blood sample would be pulled from the sample pad through the conjugation pad where the analyte of interest is labeled with a reporter molecule, bead, or particle (FIG. 1, U). The analyte of interest in the preferred embodiment is BChE, and in other embodiments AChE, or a combination of both. The analyte would be complexed in the preferred embodiment with a monoclonal antibody against BChE, and in other embodiments against AChE. Other embodiments include polyclonal antibodies against BChE and AChE (FIG. 1, U). The desired outcome is use of a high affinity antibody (either monoclonal or polyclonal in nature) that binds BChE or AChE in a species-independent manner so that the invention may be used in both human and veterinary applications. Commercially available confirmed "matched pair" anti-human-ChE antibodies to determine which most robustly bind to ChE will be used. Vendors that market already paired anti-human-BChE mAb such as: BioPorto clones HAH002-01 & HAH002-01BB-005, My BioSource clones MBS838273 & MBS838455, and Fitzgerald, clones 61-1029 & 10-1810 are examples of candidate antibodies. In other embodiments, the ChE is separated first by binding to either Test Line 1 (OP-adducted ChE), or Test Line 2 (free ChE), and secondarily labeled with a chase buffer containing reporter label-conjugated anti-ChE detection antibody. Another embodiment uses two different anti-analyte antibodies in the conjugation pad whereby one antibody recognizes only OP-bound ChE and another antibody recognizes free ChE, and both are conjugated to the same reporter molecule.

The anti-analyte antibody is conjugated to a reporter molecule such as a bead, or particle comprising a fluorescent quantum dot (Qdot), colored latex bead, gold, carbon, luminescence, or any enzyme producing a color, fluorescence, or light reaction. In the preferred embodiment, the purpose of the conjugation pad is to label all analyte molecules present in the sample with a reporter molecule. In other embodiments, the analyte is labeled with the conjugated antibody in a reaction tube with buffer (FIG. 1, E). In another embodiment, the reporter molecule is conjugated to an anti-ChE detection antibody and diluted in a "chase buffer" and house in an on-board blister pouch, or equivalent.

In a preferred embodiment, once the OP-adducted or free ChE is "tagged" with a reporter molecule (in other words, the anti-ChE antibody pre-conjugated with a reporter label binds to the OP-adducted, or free ChE in the sample), the capillary action pulls the labeled-sample through to where the first test line (zone) is located, containing in the preferred embodiment, immobilized $ZrO_2$ nanoparticles, and in other embodiments TiO2 or other nanoparticles or binding proteins that selectively bind with high affinity phosphyl moieties (FIG. 1V). Denticity refers to the number of donor groups in a single ligand that bind to a central atom in a coordination complex. Bidentate (also called didentate) ligands bind with two atoms. Titanium dioxide ($TiO_2$) and zirconium dioxide ($ZrO_2$) demonstrated the binding specificity to phosphopeptides via bidentate interactions. In another embodiment, the OP-adducted and free ChE is separated onto Test Lines 1 and 2, and then secondarily labeled in a second step by the release of a chase buffer containing reporter conjugated anti-ChE detection antibody.

The $ZrO_2$ nanoparticles will selectively bind only OP-adducted (labeled) analyte while the remainder of the sample, including free or un-adducted (labeled) analyte continues to flow through the strip (FIG. 1, W). The critical and unique component of this invention is the second test line that targets binding un-adducted (labeled) analyte (FIG. 1, M, S, X). Therefore, the second test line in the preferred embodiments will be a second anti-analyte antibody to a non-overlapping domain of the analyte protein that does not interfere with the region in which the label is bound. In the preferred embodiment, this second test line is comprised of a complimentary anti-BChE monoclonal antibody, and in other embodiments may be comprised of a complimentary anti-AChE monoclonal antibody, or anti-BChE or anti-AChE polyclonal antibodies, or a monoclonal or polyclonal antibody against the Fc portion of the conjugated label antibody (FIG. 1, X). In other words, antibodies that bind non-overlapping regions of the analyte will be used, so as to not interfere with the anti-ChE detection antibody conjugated to the reporter molecule. Vendors that market already paired anti-human-BChE mAb such as: BioPorto clones HAH002-01 & HAH002-01BB-005, may be used. Upon capturing the un-adducted analyte, the remainder of the non-specific sample devoid of analyte (as the OP-adducted ChE would bind to the first test line, and the unadducted/free ChE would bind to the second test line) will flow through the remainder of the strip to an absorption pad (1, Y and AA). In a preferred embodiment, a non-specific isotype control molecule will bind to the Control Line capture line (zone) (FIG. 1, Z) for assay quality control. The control will be a molecule known to not exist in human blood. One example of a possible control would be chicken IgY pre-conjugated with the same label intended for the analyte, and this control molecule will begin pre-loaded and dehydrated in the sample conjugation pad (e.g. fluorescence, luminescence, colloidal gold, etc.). As the entire sample passes through the conjugation pad, it rehydrates the labeled control molecule, which traverses the length of the test strip. The control will pass by both test lines and bind to a final, third, control capture line designed to bind specifically to the control molecule. If labeled chicken IgY serves as the control, then the control capture line would be comprised of a polyclonal or monoclonal antibody that specifically recognized the Fc portion of the IgY antibody. In other embodiments, the control line antibody may be oriented using Fc-lock.

Alternatively, if specifically targeting BChE, after passing through a filter stack to remove red blood cells, plasma+ running buffer will then pass through the test strip where plasma components will encounter two capture lines immobilized on a nitrocellulose membrane. First, the OP-bound BChE will adhere to the first capture line comprised of immobilized zirconium dioxide ($ZrO_2$) nanoparticles (which should bind any OP moiety). The remaining free-BChE will migrate and bind to a second capture line comprised of an anti-BChE capture antibody. A third line, the procedural control line comprised of an anti-mouse antibody, will also be deposited on the membrane. Finally, a "chase buffer" contained in a blister pack at the beginning of the cassette will be actuated. The chase buffer will rehydrate the reporter label (e.g. latex or cellulose beads or colloidal gold) conjugated with the detection anti-BChE antibody (a matched, non-overlapping pair to the capture Ab) that has been dried between the sample application port and the blister pack.

FIG. 2 depicts one embodiment of detection and interpretation of the lateral flow test strip device, with the following components:

a. The naked eye, viewing the presence or absence of Test Lines 1 and/or 2, and the presence of the Control Line b. A mobile phone camera detection, with the capability to transmit results wirelessly c. A fluorimeter, luminometer, or densitometer to capture, record, quantitate, and interpret the results and transmit results wirelessly d. A series of lines, or as a series of dots to provide a mechanism of semi-quantitation visible by the naked eye Once the OP-adducted and un-adducted analyte are complexed to the immobilized test lines 1 and 2, respectively, the results can be detected by the naked eye in the preferred embodiment (FIG. 2, a), and in additional embodiments by readers such as, but not limited to, a fluorimeter, luminometer, or densitometer to capture, record, quantitate, and interpret the results (FIG. 2, c). The reader will include a port to insert the test strip or device, if reading fluorescence a light source to excite fluorescence molecules, photo diodes to detect light emissions or color changes, optics to detect various wavelengths, interactive electronics with onboard software and firmware to provide allow interactive input of information and export of data, wi-fi connectivity capability to transmit information to databases, the cloud, or a printer, as well as Ethernet and USB ports for hardwire transmission, optional accessories such as bar code reader capability.

The test lines are intended to be interpreted based on intensity of signal at each line (FIG. 2). The signal intensity of each test line relative to the other will be used to determine OP toxicity severity. It is known that inhibition of AChE and BChE correlates with clinical signs and symptoms of OP-toxicity. Therefore, any detectable signal on the first test line (corresponding to OP-adducted analyte) indicates probable OP-exposure. The second test line representing free cholinesterase indicates the amount or remaining, functional analyte necessary for the victim's functioning and survival. The intensity of the first line relative to the second test line indicates the severity of the OP-toxicity. Taken together, the control line (the third line) must demonstrate binding, or the test is invalid. If the first line is "blank" and the second line is intense, then the user is likely unexposed, or the exposure is below the level of detection of the device, which may correlate to non-clinical significance. If the first line is intense, and the second line is blank, then the device indicates that 100% of the cholinesterase has been bound by OP and the likelihood of survival is small. We anticipate that the device will most often be used by individuals that exhibit symptoms of low level exposure that when using the device will visualize at least binding to the control line and the second, un-adducted analyte line. If any binding is detected in the first test line, the instrumented reader will calculate a percent ChE inhibition by dividing the quantitative signal of OP-bound ChE by the total amount of ChE (OP-bound ChE+free ChE). In other embodiments, the reader may produce a ratio of OP-bound versus free ChE for interpretation.

The test lines may be arranged as single lines in the preferred embodiment, or in other embodiments as a series of lines, or as a series of dots to provide a mechanism of semi quantitation visible by the naked eye (FIG. 2, d). In other embodiments the test strip results may be recorded and interpreted by scanning with a mobile phone camera (FIG. 2, c). Regardless of the reader used, the results may be printed, saved to the firmware of the device, saved to a removable storage device, or wirelessly transmitted to other storage venues, including cloud storage.

Looking now to FIG. 3, this diagram depicts one design of the lateral flow test strip device, with the following components:
A: Sample is obtained from either human or animal
B: Human sample is obtained from a finger stick
C: A disposable lancet is used to obtained sample
D: A disposable pipette is used to transfer sample to a sample tube
E: Sample is pre-diluted into a buffer comprised of labeled antibodies against the analyte or a labeled control antibody, which is incubated for several minutes.
F: Dipstick containing Test Line 1 comprised of OP-binding nanoparticles), Test Line 2 comprised of anchored anti-analyte antibodies (possibly anchored with an Fc-binding protein), and a Control Line comprised of anchored anti-control antibody antibodies (possibly anchored with an Fc-binding protein). The dipstick is incubated with the diluted sample for several minutes.
G: The dipstick (comprised of test line(s) or dots) may be visualized and interpreted via:
  a. The naked eye, viewing the presence or absence of Test Lines 1 and/or 2, and the presence of the Control Line
  b. A mobile phone camera detection, with the capability to transmit results wirelessly
  c. A fluorimeter, luminometer, or densitometer to capture, record, quantitate, and interpret the results and transmit results wirelessly The dipstick method will follow a similar labeling strategy as described above, whereby the human or animal blood, serum, or plasma sample collected in a tube will be diluted with a sample containing an antibody (or antibodies) conjugated to a label (as described in the embodiments above) (FIGS. 3, A, B, C, D, and E). Using dot-blot technology, in the preferred embodiment a nitrocellulose strip containing immobilized $ZrO_2$ nanoparticles on Test Line 1 (or in other embodiments other nanoparticles that bind phosphyl groups) and an antibody that binds the analyte or the conjugated antibody on Test Line 2 is immersed into the diluted sample containing labeled analyte (FIG. 3, F). After incubation with mild agitation, the strip is removed, rinsed with a wash buffer, and the results are captured, recorded, quantitated, and interpreted by the same modalities as described above for the LFA (FIG. 3, G(a), G(b), G(c)).

The methods and devices described herein can be used to protect first responders and at-risk personnel. Routine testing of at-risk personnel leads to early identification and treatment in the event of low-level or chronic exposure sometimes referred to as the "walking wounded." The methods and devices also improve health outcomes at the event scene. They avoid high-risk resuscitating drugs and anesthetics that can be deadly for those who have not been exposed to chemical nerve agents. For example, excessive administration of atropine in the presence of low-level, or absence of OP exposure is highly toxic (Eddleston 2004). Screening with these methods and devices will improve safety and treatment outcomes. This preferably includes screening of the "worried" or "walking well" to confirm if exposure has occurred. Exposure screening provides the most appropriate and expedient care, conserving limited therapeutic treatments for those in need (Sambursky 2015). The assays expedite treatment and improve outcomes with immediate, on-site testing and treatment. In the preferred embodiment the device may be used as a diagnostic for first responders, clinicians, law enforcement, agricultural workers, pesticide treatment professionals, veterinarians, or any other individual concerned about potential OP exposure whether occupationally, at the scene of a mass casualty event, or potential home-exposure.

An exposure producing 85% inhibition of BChE leads to compromised neurological function, requiring immediate medical care and intervention. Therefore, the clinically relevant lower limit of detection of a qualitative, optically interpreted assay should be at a chemical nerve agent blood exposure level at less than 85%. If an electronic reader is used to quantitate the results, the lower limit of detection should extend below the clinically relevant levels in order to provide a broader range of values for diagnostic interpretation. In some preferred embodiments, the methods and devices described herein detect OP agent blood exposure at inhibition levels less than or equal 85% (Sambursky 2015).

Finally, in some preferred embodiments, the devices described herein are packaged with companion antidotes and/or therapeutic drugs.

One embodiment of the instant invention includes a method of detecting a level of exposure to an organophosphorus compound via measurement of OP-bound and unbound cholinesterase levels in a sample, comprising the steps of:
  a. collecting a sample; with either a lance, a pipette, or a whole blood collection and delivery device that may or may not include an internal filter that collects the sample and then directly interlocks with the device.
  b. transferring the sample to a sample analysis device, the device comprising:
     i. a sample collection pad (in a one-step system);
     ii. at least one conjugate zone comprising an anti-analyte antibody that is conjugated with a reporter label, and a control antibody that is conjugated with a reporter label (or a one-step system), or in a two-step system an on board buffer delivery system containing a detection antibody conjugated to the reporter molecule);
     iii. a blocking and/or test zone comprising an immobilized nanoparticle or other molecule that captures the Organophosphate-bound analyte;
     iv. a second blocking and/or test zone comprising an immobilized antibody that binds to the unbound analyte; and
     v. an optional third blocking and/or control zone comprising an immobilized antibody that binds to the control molecule; wherein, when the analyte is bound by the Organophosphate in the sample it will bind to the first test line, and if the analyte is "free' from the Organophosphate it will bind to the second test line, and the control antibody will bind to the control line;
  c. detecting both the presence or absence of the binding molecule in the first test zone and the remaining analyte in the second test zone to culminate reporting a ratio of bound- and free-analyte; and'
  d. determining the level of OP exposure for an individual.

In one embodiment, the organophosphorus is selected from the group including, but not limited to, a chemical nerve agent, a pesticide, or a combination thereof. In another embodiment, the sample is selected from the group including, but not limited to, blood, plasma, whole blood, serum, urine, tears, saliva cerebrospinal fluid, or a combination thereof and the sample is from either a human or an animal. In yet another embodiment, the conjugation pad/zone or chase buffer is comprised of a labeled anti-analyte antibody and an optional labeled control molecule, wherein the anti-analyte antibody and the control molecule are each conjugated with a reporter label.

In one embodiment, when the analyte is bound by the Organophosphate in the sample it will bind to the first test line, and if the analyte remains unbound from the Organophosphate it will bind to the second test line, and the optional control molecule will bind to the optional control line providing a base-line free result. In another embodiment, detecting the presence or absence of the OP-bound analyte in the first test zone and the remaining unbound analyte in the second test zone results in reporting a ratio of bound- and free-analyte resulting in an assay which does not require a pre-determined base-line measurement. In still another embodiment, the sample analysis device is a lateral flow test strip device or dipstick device. In yet another embodiment, the analyte is selected from the group including Acetylcholinesterase (AChE) and Butylcholinesterase (BChE). In still another embodiment, the Organophosphate is a toxicant with an organophosphate molecule, including but not limited to:
  (a) OP chemical warfare agents
     i. G series: tabun, sarin, soman, cyclosarin
     ii. GV series: novichok, GV
     iii. V series: VE, VG, VM, VX
  (b) OP pesticides
  (c) Other organophosphorus toxicants (i.e. herbicides, industrial chemicals) the binding molecule is a toxicant with a carbamate molecule in origin.

In one embodiment, the anti-analyte antibody is a monoclonal or polyclonal antibody raised against human or animal AChE or BChE. In another embodiment, the label conjugated to the anti-analyte antibody is one of the following types of labels: Quantum dot (Qdot), Latex particle, Colloidal gold (+/− silver enhancement), Colloidal carbon, Fluorescent probe (e.g. xanthene dyes, cyanine dyes, lanthanide complexes), Bioluminescent, or a combination thereof. In yet another embodiment, the control antibody is a chicken IgY raised against a non-human or animal protein conjugated with the same label used to conjugate the anti-analyte antibody. In still another embodiment, the blocking material may be bovine serum albumin, milk protein, gelatin, or any other commercially available blocking agent. In still another embodiment, the immobilized nanoparticle in test zone one that binds the Organophosphate is zirconium dioxide ($ZrO_2$), titanium dioxide ($TiO_2$), or any other nanoparticle that preferentially binds phosphyl moieties. In yet another embodiment, the immobilized nanoparticle in test zone one that specifically binds the carbamate-binding molecule.

In one embodiment, the immobilized antibody in test zone two that binds to the analyte+conjugated anti-analyte antibody (from the conjugation zone) is an anti-AChE antibody or anti-BChE antibody (that does not interfere with the binding site of the already bound conjugated anti-analyte antibody), or a monoclonal or polyclonal antibody (raised in any animal species) against the Fc-receptor domain of the host species used to produce the conjugated anti-analyte antibody. In another embodiment, the immobilized antibody in the control zone that binds to the conjugated chicken IgY antibody (from the conjugation zone) is a monoclonal or polyclonal antibody (raised in any animal species) against the Fc-receptor domain of chicken IgY antibody. In still another embodiment, "Fclock" recombinant protein may be used to bind and orient in a "right-side-up" manner the immobilized antibodies on the conjugated label, for test zone two, and for the control zone. In yet another embodiment, the method of detection may be via visual inspection of the test lines, or quantitative detection using a handheld or other reader. In still another embodiment, the recording of information from may be by digital photograph or scan using the camera from a cellular device. In yet another embodiment, the quantitative detection using a handheld reader is an ESE-Quant, GoldScan, or FluoScan from ESE GmbH (OEM partner), or an equivalent detector.

One embodiment of the instant invention may include the following device:
1. A sample analysis device used to detect a level of exposure of organophosphorus within a sample comprising:
   a. a sample collection pad;

b. one or more conjugation pads/zones; and
c. one or more blocking/test zones.
d. two-step system with an on-board buffer delivery system containing a chase buffer
2. The device of claim 1 wherein the organophosphorus is selected from the group including, but not limited to, a chemical nerve agent, a pesticide, or a combination thereof.
3. The device of claim 1 wherein the sample to be tested is selected from the group including, but not limited to, blood, plasma, whole blood, serum, urine, tears, saliva, cerebrospinal fluid, or a combination thereof.
4. The device of claim 3 wherein the sample is from either a human or an animal.
5. The device of claim 1 wherein the conjugation pad/zone is comprised of:
a labeled anti-analyte antibody; and
an optional labeled control molecule.
6. The device of claim 1 wherein said anti-analyte antibody and said control antibody are each conjugated with a reporter label.
7. The device of claim 1 wherein said sample analysis device includes
a first blocking/test zone which includes an immobilized nanoparticle or other molecule which captures the Organophosphate;
a second blocking/test zone which includes an immobilized antibody which binds to the analyte; and
a third blocking/test zone which includes an immobilized antibody that binds to the control antibody.
8. The device of claim 7 wherein when the analyte is bound by the Organophosphate in the sample it will bind to the first test zone, and if the analyte remains unbound from the Organophosphate it will bind to the second test zone, and the optional control molecule will bind to the optional control zone providing a base-line free result.
9. The device of claim 7 wherein detecting the presence or absence of the OP-bound analyte in the first test zone and the remaining unbound analyte in the second test zone results in reporting a ratio of bound- and free-analyte resulting in an assay which does not require a predetermined base-line measurement.
10. The device of claim 1, wherein the sample analysis device is a lateral flow test strip device or dipstick device.
11. The device of claim 1, wherein the analyte is selected from the group including:
a. Acetylcholinesterase (AChE)
b. Butylcholinesterase (BChE)
12. The device of claims 1 and 11, wherein the Organophosphate is a toxicant with an organophosphate molecule, including but not limited to:
a. OP chemical warfare agents
i. G series: tabun, sarin, soman, cyclosarin
ii. GV series: novichok, GV
iii. V series: VE, VG, VM, VX
b. OP pesticides
c. Other organophosphorus toxicants (i.e. herbicides, industrial chemicals).
13. The device of claims 1 and 11 wherein the binding molecule is a toxicant with a carbamate molecule.
14. The device of claim 1, wherein the anti-analyte antibody is a monoclonal or polyclonal antibody raised against human or animal AChE or BChE.
15. The device of claim 1, wherein the label conjugated to the anti-analyte antibody is one of the following types of labels:
a. Quantum dot (Qdot)
b. Latex particle
c. Colloidal gold (+/− silver enhancement)
d. Colloidal carbon
e. Fluorescent probe (e.g. xanthene dyes, cyanine dyes, lanthanide complexes)
f. Bioluminescent.
16. The device of claims 1 and 15, wherein the control antibody is a chicken IgY raised against a non-human or animal protein conjugated with the same label used to conjugate the anti-analyte antibody.
17. The device of claim 1, wherein the blocking material may be bovine serum albumin, milk protein, gelatin, or any other commercially available blocking agent.
18. The device of claim 1, wherein the immobilized nanoparticle in test zone one that binds the Organophosphate is zirconium dioxide ($ZrO_2$), titanium dioxide ($TiO_2$), or any other nanoparticle that preferentially binds phosphyl moieties.
19. The device of claim 7, wherein the immobilized nanoparticle in test zone one that specifically binds the carbamate-binding molecule.
20. The device of claim 7, wherein the immobilized antibody in test zone two that binds to the analyte+conjugated anti-analyte antibody (from the conjugation zone) is an anti-AChE antibody or anti-BChE antibody (that does not interfere with the binding site of the already bound conjugated anti-analyte antibody), or a monoclonal or polyclonal antibody (raised in any animal species) against the Fc-receptor domain of the host species used to produce the conjugated anti-analyte antibody.
21. The device of claim 7, wherein the immobilized antibody in the control zone that binds to the conjugated chicken IgY antibody (from the conjugation zone) is a monoclonal or polyclonal antibody (raised in any animal species) against the Fc-receptor domain of chicken IgY antibody.
22. The device of claims 1-21 wherein "Fclock" recombinant protein may be used to bind and orient in a "right-side-up" manner the immobilized antibodies on the conjugated label, for test zone two, and for the control zone.
23. The device of claim 1, wherein the method of detection may be via visual inspection of the test lines, or quantitative detection using a handheld or other reader.
24. The device of claim 23, wherein the recording of information may be by digital photograph or scan using the camera from a cellular device.
25. The device of claim 23, wherein the quantitative detection using a handheld reader is an ESE-Quant, GoldScan, or FluoScan from ESE GmbH (OEM partner), or an equivalent detector.
One embodiment of the instant invention may include the following method:
26. A method of detecting a level of exposure to organophosphorus comprising the steps of:
a. collecting a sample;
b. transferring the sample to a sample analysis device comprising
i. a sample collection pad;
ii. one or more conjugation pads/zones;
iii. one or more blocking/test zones;
iv. one or more buffer delivery systems
c. detecting the presence or absence of organophosphorus; and
d. determining the level of OP exposure for an individual.
27. The method of claim 26 wherein the organophosphorus is selected from the group including, but not limited to, a chemical nerve agent, a pesticide, or a combination thereof.

28. The method of claim 26 wherein the sample is selected from the group including, but not limited to, blood, plasma, whole blood, serum, urine, tears, saliva, cerebrospinal fluid, or a combination thereof.

29. The method of claim 28 wherein the sample is from either a human or an animal.

30. The method of claim 26 wherein the conjugation pad/zone is comprised of:
a labeled anti-analyte antibody; and
an optional labeled control molecule.
A conjugated anti-analyte detection antibody housed in an on-board buffer delivery system such as a foil blister pouch, a breakable ampoule, or equivalent.

31. The method of claim 30 wherein the anti-analyte antibody and the control molecule are each conjugated with a reporter label.

32. The method of claim 26 wherein the sample analysis device includes
a first blocking/test zone which includes an immobilized nanoparticle which captures the OP-bound analyte and
a second blocking/test zone which includes an immobilized antibody which binds to the non-OP bound free analyte;
an optional third blocking/test zone which includes an immobilized antibody that binds to the control molecule.

33. The method of claim 32 wherein when the analyte is bound by the Organophosphate in the sample it will bind to the first test line, and if the analyte remains unbound from the Organophosphate it will bind to the second test line, and the optional control molecule will bind to the optional control line providing a base-line free result.

34. The method of claim 33 wherein detecting the presence or absence of the OP-bound analyte in the first test zone and the remaining unbound analyte in the second test zone results in reporting a ratio of bound- and free-analyte resulting in an assay which does not require a predetermined base-line measurement.

35. The method of claim 26, wherein the sample analysis device is a lateral flow test strip device or dipstick device.

36. The method of claim 26, wherein the analyte is selected from the group including:
c. Acetylcholinesterase (AChE)
d. Butylcholinesterase (BChE)

37. The method of claims 26 and 36, wherein the Organophosphate is a toxicant with an organophosphate molecule, including but not limited to:
e. OP chemical warfare agents
   i. G series: tabun, sarin, soman, cyclosarin
   ii. GV series: novichok, GV
   iii. V series: VE, VG, VM, VX
f. OP pesticides
g. Other organophosphorus toxicants (i.e. insecticides, industrial chemicals).

38. The method of claims 26 and 36 wherein the binding molecule is a toxicant with a carbamate molecule.

39. The method of claim 26, wherein the anti-analyte antibody is a monoclonal or polyclonal antibody raised against human or animal AChE or BChE.

40. The method of claim 26, wherein the label conjugated to the anti-analyte antibody is one of, but not limited to, the following types of labels:
g. Quantum dot (Qdot)
h. Latex particle
i. Colloidal gold (+/− silver enhancement)
j. Colloidal carbon
k. Fluorescent probe (e.g. xanthene dyes, cyanine dyes, lanthanide complexes)
l. Bioluminescent molecule.

41. The method of claims 26 and 40, wherein the control antibody is a chicken IgY raised against a non-human or animal protein conjugated with the same label used to conjugate the anti-analyte antibody.

42. The method of claim 26, wherein the blocking material may be bovine serum albumin, milk protein, gelatin, or any other commercially available blocking agent.

43. The method of claim 26, wherein the immobilized nanoparticle in test zone one that binds the Organophosphate is zirconium dioxide ($ZrO_2$), titanium dioxide ($TiO_2$), or any other nanoparticle that preferentially binds phosphyl moieties.

44. The method of claim 32, wherein the immobilized nanoparticle or molecule in test zone one that specifically binds the carbamate bound analyte.

45. The method of claim 32, wherein the immobilized antibody in test zone two that binds to the analyte+either unconjugated (if a 2-step system) or conjugated anti-analyte antibody (from the conjugation zone in a one-step system) is an anti-AChE antibody or anti-BChE antibody (that does not interfere with the binding site of the already bound conjugated anti-analyte antibody), or a monoclonal or polyclonal antibody (raised in any animal species) against the Fc-receptor domain of the host species used to produce the conjugated anti-analyte antibody.

46. The method of claim 32, wherein the immobilized antibody in the control zone that binds to the conjugated chicken IgY antibody (from the conjugation zone) is a monoclonal or polyclonal antibody (raised in any animal species) against the Fc-receptor domain of chicken IgY antibody.

47. The method of claims 26-46 wherein "Fclock" recombinant protein may be used to bind and orient in a "right-side-up" manner the immobilized antibodies on the conjugated label, for test zone two, and for the control zone.

48. The method of claim 26, wherein the method of detection may be via visual inspection of the test lines, or quantitative detection using an instrumented reader.

49. The method of claim 48, wherein the recording of information may be by digital photograph or scan using the camera from a cellular device.

50. The method of claim 28, wherein the quantitative detection using a handheld reader is an ESE-Quant, GoldScan, or FluoScan from ESE GmbH (OEM partner), or an equivalent detector.

Any method described herein may incorporate any design element contained within this application and any other document/application incorporated by reference herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The present invention may be embodied in other forms without departing from the spirit and the essential attributes thereof, and, accordingly, reference should be made to the appended claims, rather than to the foregoing specification, as indicating the scope of the invention. The invention illustratively discloses herein suitably may be practiced in the absence of any element which is not specifically disclosed herein.

We claim:
1. A method of detecting a level of exposure to an organophosphorus compound via measurement of organophosphate (OP) bound and unbound cholinesterase levels in a sample, comprising the steps of:
   a. collecting a sample;
   b. transferring the sample to a sample analysis device, the device comprising:
      i. a sample collection pad;
      ii. at least one conjugate zone comprising an anti-analyte antibody that is conjugated with a reporter label, and a control antibody that is conjugated with a reporter label;
         wherein the anti-analyte antibody is selected from the group consisting of:
            a. anti-acetylcholinesterase (AChE) antibody
            b. anti-butylcholinesterase (BChE) antibody;
      iii. a blocking and/or test zone comprising an immobilized nanoparticle or other molecule that captures the Organophosphate-bound analyte;
      iv. a second blocking and/or test zone comprising an immobilized antibody that binds to the unbound analyte; and
      v. an optional third blocking and/or control zone comprising an immobilized antibody that binds to a control molecule; wherein, when the analyte is bound by the Organophosphate in the sample it will bind to the first blocking and/or test zone, and if the analyte is "free' from the Organophosphate it will bind to the second blocking and/or test zone, and the control antibody will bind to the third blocking and/or control zone;
   c. detecting both the presence or absence of the binding molecule in the first blocking and/or test zone and the remaining analyte in the second blocking and/or test zone to culminate reporting a ratio of bound- and free-analyte; and
   d. determining the level of OP exposure for an individual.

2. The method of claim 1 wherein the sample is selected from the group consisting of: blood, plasma, whole blood, serum, urine, tears, saliva cerebrospinal fluid, or a combination thereof.

3. The method of claim 1 wherein the conjugation zone is comprised of:
   a labeled anti-analyte antibody; and
   an optional labeled control molecule.

4. The method of claim 1 wherein when the analyte is bound by the Organophosphate in the sample, it will bind to the first blocking and/or test zone, and if the analyte remains unbound from the Organophosphate it will bind to the second test line, and the optional control molecule will bind to the optional control line providing a base-line free result.

5. The method of claim 1 wherein detecting the presence or absence of the OP-bound analyte in the first test zone and the remaining unbound analyte in the second test zone results in reporting a ratio of bound- and free-analyte resulting in an assay which does not require a pre-determined base-line measurement.

6. The method of claim 1, wherein the blocking material is selected from bovine serum albumin, milk protein, gelatin, or any similar blocking material.

7. The method of claim 1, wherein the immobilized nanoparticle in test zone one that binds the Organophosphate is zirconium dioxide ($ZrO_2$), titanium dioxide ($TiO_2$), or any other nanoparticle that preferentially binds phosphyl moieties.

8. The method of claim 1, wherein the immobilized antibody from the conjugation zone is an anti-AChE antibody or anti-BChE antibody that does not interfere with the binding site of the already bound conjugated anti-analyte antibody, or a monoclonal or polyclonal antibody against the Fc-receptor domain of the host species used to produce the conjugated anti-analyte antibody.

9. The method of claim 1, wherein the immobilized antibody from the conjugation zone is a monoclonal or polyclonal antibody against the Fc-receptor domain of chicken IgY antibody.

10. A sample analysis device used to detect a level of exposure of organophosphorus within a sample comprising:
    a sample collection pad;
    at least one conjugate zone comprising an anti-analyte antibody that is conjugated with a reporter label, and a control antibody that is conjugated with a reporter label;
       wherein the anti-analyte antibody is selected from the group consisting of:
          a. anti-acetylcholinesterase (AChE) antibody
          b. anti-butylcholinesterase (BChE) antibody;
    a blocking and/or test zone comprising an immobilized nanoparticle or other molecule that captures the Organophosphate-bound analyte;
    a second blocking and/or test zone comprising an immobilized antibody that binds to the unbound analyte; and
    an optional third blocking and/or control zone comprising an immobilized antibody that binds to the control molecule; wherein, when the analyte is bound by the Organophosphate in the sample it will bind to the first blocking and/or test zone, and if the analyte is "free' from the Organophosphate it will bind to the second blocking and/or test zone, and the control antibody will bind to the third blocking and/or control zone ;
    wherein the presence or absence of a first analyte is detected in the first blocking and/or test zone and the presence or absence of the remaining analyte is detected in the second blocking and/or test zone to culminate reporting a ratio of bound- and free-analyte; and
    wherein the level of OP exposure is determined for an individual.

11. The device of claim 10 wherein the sample is selected from the group consisting of: blood, plasma, whole blood, serum, urine, tears, saliva cerebrospinal fluid, or a combination thereof.

12. The device of claim 10 wherein when the analyte is bound by the Organophosphate in the sample, it will bind to the first blocking and/or test zone, and if the analyte remains unbound from the Organophosphate it will bind to the second test line, and the optional control molecule will bind to the optional control line providing a base-line free result.

13. The device of claim 10 wherein detecting the presence or absence of the OP-bound analyte in the first blocking and/or test zone and the remaining unbound analyte in the second test zone results in reporting a ratio of bound- and free-analyte resulting in an assay which does not require a pre-determined base-line measurement.

14. The device of claim 10, wherein the wherein the analyte is selected from the group including:
    a. Acetylcholinesterase (AChE)
    b. Butylcholinesterase (BChE).

15. The device of claim 10, wherein the blocking material is selected from bovine serum albumin, milk protein, gelatin, or any similar blocking material.

16. The device of claim 10, wherein the immobilized nanoparticle in test zone one that binds the Organophosphate is zirconium dioxide ($ZrO_2$), titanium dioxide ($TiO_2$), or any other nanoparticle that preferentially binds phosphyl moieties.

17. The device of claim 10, wherein the immobilized antibody from the conjugation zone is an anti-AChE antibody or anti-BChE antibody that does not interfere with the binding site of the already bound conjugated anti-analyte antibody, or a monoclonal or polyclonal antibody against the Fc-receptor domain of the host species used to produce the conjugated anti-analyte antibody.

18. The device of claim 10, wherein the immobilized antibody from the conjugation zone is a monoclonal or polyclonal antibody against the Fc-receptor domain of chicken IgY antibody.

\* \* \* \* \*